United States Patent [19]

Sommervold

[11] 4,043,756

[45] Aug. 23, 1977

[54] CALIBRATION IN AN AUTOMATIC CHEMICAL TESTING APPARATUS

[75] Inventor: David E. Sommervold, Houston, Tex.

[73] Assignee: Hycel, Inc., Houston, Tex.

[21] Appl. No.: 758,055

[22] Filed: Dec. 29, 1976

[51] Int. Cl.$^2$ .................... G01N 33/16; G01N 21/24; G01N 21/58

[52] U.S. Cl. .............................. 23/230 R; 23/253 R; 235/151.35

[58] Field of Search ............. 23/230 R, 230 B, 253 R, 23/259; 356/36, 39; 235/151.35

[56] References Cited

U.S. PATENT DOCUMENTS

| 3,697,224 | 10/1972 | Means | 23/253 X |
| 3,725,204 | 4/1973 | Marshall, Jr. et al. | 23/253 X |
| 3,861,877 | 1/1975 | Matharani et al. | 23/253 X |
| 3,873,273 | 3/1975 | Moran et al. | 23/259 X |
| 3,874,850 | 4/1975 | Sorensen et al. | 23/253 X |

*Primary Examiner*—R.E. Serwin

*Attorney, Agent, or Firm*—Robert P. Cogan; Timothy L. Burgess

[57] ABSTRACT

In an automatic chemical testing apparatus calibration values obtained from readout signals of analysis means must be stored for use in prior art calculating means for processing of subsequent readout signals of samples containing unknown quantities of substances in a medium. Improved means are provided for selecting the calibration values, namely a blank value and a reference value. A plurality of pairs of blank and reference samples are processed. The blank samples have known zero or baseline levels or concentrations of substances, and the reference samples have known concentration levels of each substance. These known values are stored for comparison to processed values obtained by processing the readout signals obtained in response to analysis of the blank and reference samples. The validity of each such readout signal as a calibration value is determined by the successfulness of the comparison. The most current successful blank and reference signals are selected as the calibration values. For verifying validity, the selected calibration values are utilized for processing signals obtained from a calibration control sample for which known substance concentration values are stored. A blank, reference and calibration control sample are processed as above at a later time for updating the calibration values during continued operation of the apparatus.

22 Claims, 8 Drawing Figures

| POSITION | CONTENTS |
|---|---|
| 101 | BLANK |
| 102 | REF. |
| 103 | BLANK |
| 104 | REF. |
| 105 | BLANK |
| 106 | REF. |
| 107 | CAL. CONTROL |
| 108 | SAMPLE |
| ↓ | ↓ |
| 116 | SAMPLE |
| 117 | BLANK |
| 118 | REF. |
| 119 | CAL. CONTROL |
| 120 | SAMPLE |
| ↓ | ↓ |

CALIBRATION IN AN AUTOMATIC CHEMICAL TESTING APPARATUS

BACKGROUND OF THE INVENTION

The present invention relates to automatic chemical testing apparatus and more particularly to means for calibrating signal processing circuitry which provides output signals indicative of concentrations of substances in an analyzed sample.

A suitable environment contemplated for the present invention is disclosed in commonly assigned U.S. Pat. No. 3,728,079 issued Apr. 17, 1973 to John J. Moran, the disclosure of which is incorporated herein by reference. U.S. Pat. No. 3,622,279 issued Nov. 23, 1971 to John J. Moran, also commonly assigned and having its disclosure incorporated herein by reference, is particularly directed toward means for providing readout signals in response to reacted contents in reaction containers.

In the type of apparatus under consideration, aliquots of a sample generally comprising human serum are each dispensed into a reaction container and reagents are added thereto. After sufficient incubation, a reading is made of the contents of the reaction container to provide a signal indicative of a particular parameter. In the preferred form, the reading is made spectrophotometrically, and an analog signal indicative of optical density is provided. In order to determine concentration of the particular substance for which analysis is being made of the particular aliquot, the optical density reading must be translated into a reading indicative of concentration units of a substance.

A means of providing an output indicative of concentration units is by the use of the electrical circuitry and printout means. The circuitry utilizes known techniques to process the analog readout signal indicative of optical density into an output signal for provision to printing or display means indicative of concentration units. The circuitry employs a linear curve relating optical density to concentration of the substance which has been empirically determined. (Curve fitting techniques are well-known in the art, and do not form a part of the present invention. Therefore, curve fitting techniques and circuitry are not discussed in great detail herein.)

However, in order to use the curves which have been provided by prior art curve fitting techniques successfully, reliable information must be provided for calibrating the curve. Calibrating the curve means taking an established curve to be utilized in a circuit and setting the zero intercept and slope thereof or providing a result equivalent thereto. Calibrating the curve is done by use of calibration samples. A sample called a blank is used to produce a signal which should result in an output signal at a zero or baseline level, and adjustment is made such that a proper output is thus produced. A sample called a reference having known concentrations of substances therein is measured, and the slope of the curve is adjusted so the output signal is at a proper readout value determined by the known value associated with the reference sample.

The function of calibrating output circuitry has been successfully performed in the past manually, for example, by means of operators observing meters indicative of output signals and performing manual potentiometer adjustments. A value based on reading the blank, or a blank value, and value based on a reading of the reference, or a reference value, form the basis for validity of outputs processed by the processing circuitry. In this manner, calibration values are provided to signal processing circuitry. While this form of adjustment is effective and reliable, it is even more desirable to provide a system capable of providing calibration values to prior art processing circuitry without operator intervention. It is further desirable to provide a system capable of periodically checking the validity of calibration values it is utilizing.

SUMMARY OF THE INVENTION

It is therefore an object of the present invention to provide in an automatic chemical testing apparatus means for providing calibration values to processing circuitry which processes parameter-indicative signals according to a curve which must be calibrated.

It is also an object of the present invention to provide calibration means for generating a plurality of signals each indicative of a calibration value and for selecting one of said signals for use as the calibration value based on successful comparison with predetermined suitable values resulting from use of the signal as a calibration value.

It is an additional object of the present invention to provide a means for generating signals which in effect are indicative of desired zero intercepts and slope for provision to curve calibration circuitry and for testing the validity of use of the signals prior to processing of unknown samples.

It is a further object of the present invention to provide in a system of the type described means for responding to drift in calibration values.

It is a specific object of the present invention to provide an apparatus of the type described for relating optical density of a sample to concentration units of a substance contained therein.

It is a further object to provide in an apparatus of the type described means for providing data indicative of parameters for a sample when the calibration values are not valid and means for detecting invalidity of calibration values.

It is another object of the present invention to provide a method and apparatus of the type described in which calibration values supplied to processing means may be checked and updated periodically.

Briefly stated, in accordance with the present invention, in an automatic chemical testing apparatus calibration values obtained from readout signals of analysis means are provided for storage and use in prior art calculating means for processing of subsequent readout signals of samples containing unknown quantities of substances in a medium. The calibration values are a blank value and a reference value. A plurality of pairs of blank and reference samples are processed. The blank samples have known zero or baseline levels of concentrations of substances, and the reference samples have known concentration levels of each substance. These known values are stored for comparison to processed values obtained by processing the readout signals obtained in response to analysis of the blank and reference samples. The validity of each such readout signal as a calibration value is determined by the successfulness of the comparison. The most current successful blank and reference signals are selected as the calibration values. For verifying validity, the selected calibration values are utilized for processing signals obtained from a calibration control sample for which known substance concentration values are stored. A blank, reference and calibration control sample are processed as above at a later time for updating the calibration values during continued operation of the apparatus.

BRIEF DESCRIPTION OF THE DRAWINGS

The means by which the foregoing object and features of invention are achieved are pointed out with particularity in the claims forming the concluding portion of the specification. The invention, both as to its organization and manner of operation, may be further understood by reference to the following description taken in connection with the following drawings.

Of the drawings.

DESCRIPTION OF THE PREFERRED EMBODIMENT

Figure 1:
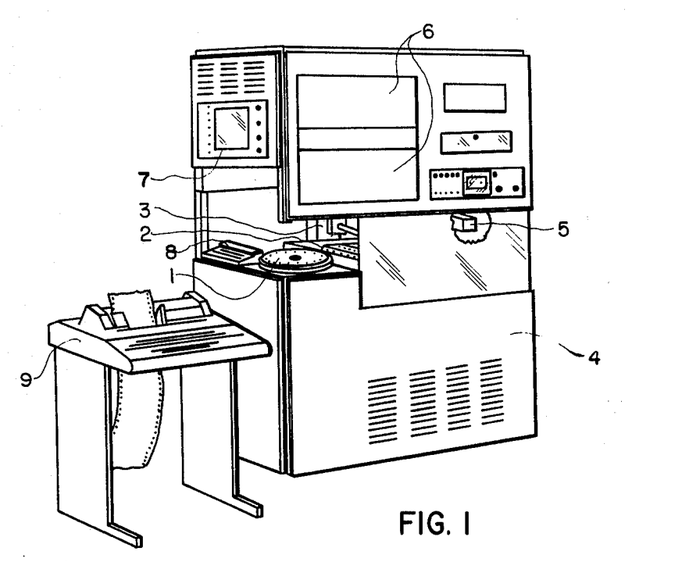
FIG. 1 is an illustration of an automatic chemical testing apparatus incorporating the present invention.

FIG. 1 is an illustration of an automatic chemical testing analyzer incorporating the present invention while the present invention may find application in many forms of chemical analyzers, the preferred environment is the analyzer described in the above-cited patents to Moran. Reference should be had thereto for a further description of the analyzer of FIG. 1. Briefly stated, samples are successively obtained from a sample source 1 and delivered to reaction containers in a reaction loop 2 having incubation and reagent dispensing stations 3. Reagents are supplied thereto from reagent supply means 4. At a further end of the reaction loop 2, aspiration and analysis means 5 withdraw reacted contents from reaction containers in the conveyor 2 and provide photometric readouts indicative of optical density of each sample. Control means 6 are provided for selecting which tests are to be performed on each sample and consequently for controlling which reagents are dispensed into each reaction container if any in the conveyor 2. In the present embodiment, display means 7, keyboard means 8, and printout means 9 are provided. The display means 7 and printout means 9 of the present embodiment replace the chart recorder of the embodiment of the above-cited patents to Moran. The readout means 5 provide a plurality of readout signals, each indicative of optical density of a reacted aliquot in each channel for one sample during a machine cycle. It has been prior procedure to process three calibration pairs of samples, each pair consisting of a blank sample and a reference sample, readout signal from one sample being processed during each of six successive cycles. This is accomplished by providing the six successive samples positioned to be taken in turn at the sample source 1.

The calibration sets are used to relate concentration values indicated by the level of analog signals coming from the readout block 5 to known values predetermined for each blank and reference sample. This is done separately for each channel of the analyzer in FIG. 1, there are 17 chemistry channels, each providing a different analog output indicative of a particular substance in a sample. These calculations referred to here and below are performed separately and in an identical manner for each channel.

Figure 2:
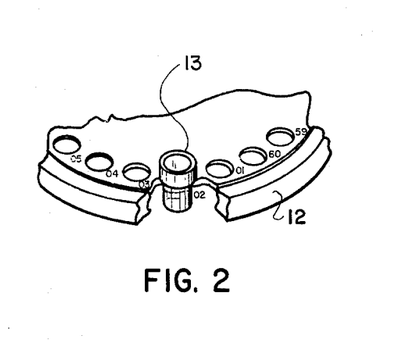
FIG. 2 is a partial, detailed view of the sample table in FIG. 1 illustrating the placement of samples therein.
Figure 3:
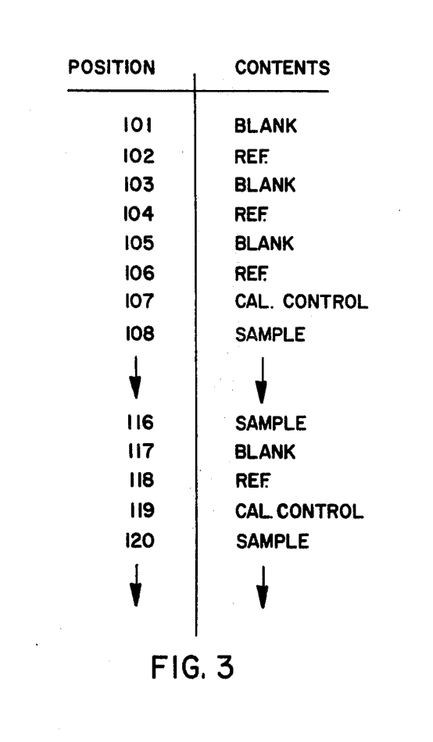
FIG. 3 is a chart illustrating one preferred order of presentation of samples of different types to the automatic chemical testing apparatus.

FIG. 2 is a partial detailed view of the sample table 1 illustrating recesses 12 for receiving sample containers 13. In a preferred embodiment, the sample table 1 includes sixty recesses 12. As illustrated in FIG. 2, each recess may be numbered 01, 02, . . . Each sample may then be referred to by its position in the table and by the revolution the sample table 1 makes. This takes into account that sample containers 13 from which samples have been withdrawn for processing are replaced so that a further sample container 13 is presented in the recess 12 on a subsequent revolution of the sample table 1. A sequence of samples in utilizing this numbering convention is illustrated in FIG. 3. FIG. 3 is a chart illustrating position versus contents of a particular sample container 13. In the preferred embodiment, three repeating pairs of blank and reference serum samples are used, followed by a calibration control sample, followed by an interval of patient, or unknown, samples. Thereafter a recalibration set may be provided including a blank, reference, and calibration control. A blank is a serum sample prepared having zero or baseline values for various substances for which testing will be performed. A reference in the present context is utilized to mean a sample having a fixed amount of each substance to fall in a proper place in the calibration curve. Calibration control represents a sample which is used as a standared to test the results of the calibration. The blank, reference, and calibration control samples are produced in particular lots, and assay sheets are prepared for each lot indicating the result which should be obtained.

Figure 4:
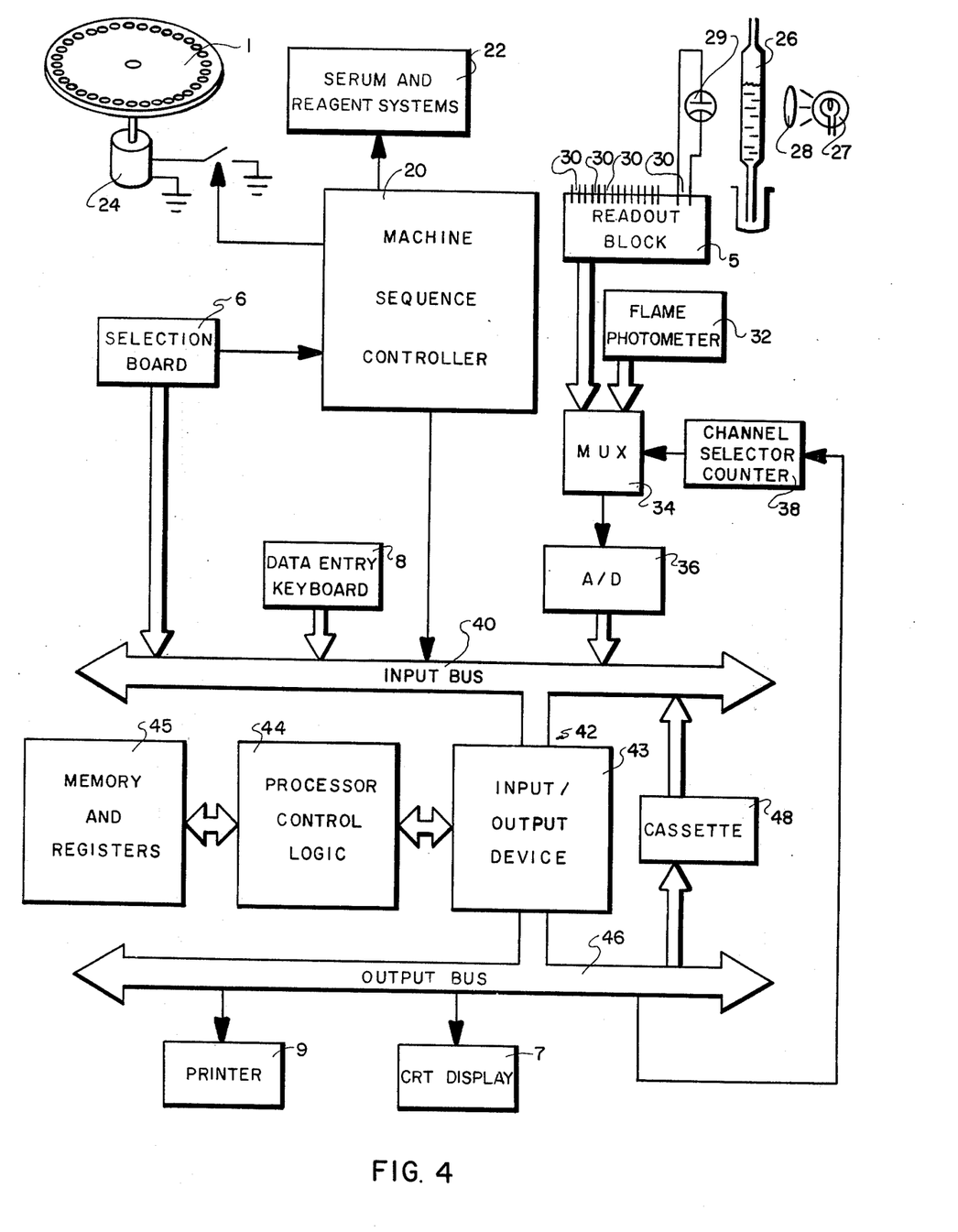
FIG. 4 is a block diagrammatic representation of the circuitry of the present invention.

FIG. 4 is a block diagrammatic representation of an apparatus incorporating the improved calibration system of the present invention. System elements briefly referred to here which perform the functions of prior art analyzers are more fully described in the above-cited patents to Moran.

Referring to FIG. 4, machine functions are controlled and coordinated by a machine sequence controller 20 which provides timing and enabling signals to various components. The machine sequence controller 20 may be made in a hard wired form as disclosed in the above-cited patents to Moran, or may include mini-computer or microprocessor circuitry. The machine sequence controller 20 provides timing signals to serum and reagent systems 22. The serum and reagent systems 22 include the reagent dispensing station 3, reagent supply means 4, and the conveyor carrying the reaction containers. The machine sequence controller 20 further provides signals for energizing a motor 24 for periodically indexing the sample source 1. The selection board 6 is also connected to the machine sequence controller 20 which translates test selections reflected by the pressing of test selection buttons in the control means 6 into command signals at appropriate times for dispensing reagents into preselected reaction containers.

As described in the patents to Moran, readout cuvettes 26 are provided in the analysis means 5 (FIG. 1). A light source 27 shines through a lens 28 through reacted contents in the readout cuvette 26 to provide a resulting amount of light at a particular wave-length to a sensor 29 connected to a set of terminals 30. For simplicity of the drawing, a number of sets of terminals 30 are illustrated, each for connection to a photo-cell 29 for making a similar form of measurement. The wavelength to which the photocell 29 is made sensitive, for example, as by appropriate filtering, is selected in accordance with the particular chemistry being performed. The amount of light at the wavelength is a Beer's law function of the optical density of the reacted contents in the readout cuvettes 26. Consequently, the analog signal appearing at the terminal 30 is indicative of the concentration of the substance being tested for in the particular channel corresponding to the particular readout cuvette 26. Additionally, a flame photometer 32 may provide output readings indicative of substances determined by flame photometric means rather than by spectrophotometric means through liquid in cuvettes. Of course, other forms of transducers to provide chemistry results may be utilized.

The analog outputs are all supplied to a multiplexer 34 which supplies analog outputs one at a time to an analog-to-digital converter 36. The multiplexer may include a decoder connected to a channel selector counter 38 to pass the signal corresponding to a channel indicated by the output of the channel selector counter 38. While this is a preferred form, other means may be used for providing digital signals. Some other form of transducer for providing digital rather than analog output could be used and polling or interrupt techniques can be used for translating the results to a point corresponding to the output of the analog digital converter 36. The present embodiment is illustrated since it is a very effective and simple form of obtaining the data. However, the means for gathering the raw data presented to the apparatus described below forms no part of the present invention, and could easily be replaced by other means well-known in the art.

Outputs are provided to an input data bus 40 to data translating means 42. The translating means 42 may, for example, comprise such commercially available apparatus as the Alpha 16 Computer of LSI-II minicomputers manufactured by Computer Automation Inc., Irvine, Cal. Depending on the amount of data to be handled, microprocessors such as the Motorola M6800 or Texas Instruments 8080 could also be utilized. The computing means 42 comprises a standard input/output circuit 43, processor and control logic circuit 44, and memory and register banks 45, all interconnected for processing data at appropriate times as described below. The input/output device 43 is connected to an output bus 46 which provides output data to the cathode ray tube display 7 and printer 9 (FIG. 1) as well as an input to the channel selector counter 38 and a cassette unit 48. The cassette unit 48 may also be used to provide data to the input bus 40. The machine sequence controller, data entry keyboard 8, and selection board 6 are all connected to the input bus 6 for conventional synchronization and coordination of data handling functions.

The structure and operation of the apparatus is described in FIGS. 5-8, which are flow charts. The actual coding of a computer program to interconnect the computer in accordance with the present invention, is a direct function of the flow-chart. Those skilled in the art may translate the flow charts of FIGS. 5-8 into computer programs without experimentation by well-known techniques. For example, translation of a flow chart into a computer program without experimentation is illustrated in John G. Wester & Willian D. Simpson, *Software Design for Microprocessors*, (Texas Instruments, Dallas, Tex. 1976). The provision of a flow chart rather than a particular program listing will enable those skilled in the art to select their own computer. Program steps are translated into particular program language, for example, through the use of the manual associated with a particular computer. If one desires to implement the present invention on an Alpha-16 computer, reference may be had to *Alpha* 16 & Naked Mini ® 16 Computer Reference Manual (Computer Automation, Inc., Newport Beach, Cal. 1971). For programming a Motorola M-6800 Microprocessor, reference may be had to *M-6800 Microprocessor Programming Manual* (Motorola, Inc., 1975). Many different computers may be substituted for the computing means 42 of FIG. 4 to provide circuitry operating in accordance with the present invention.

Qualitatively, the following will be done. Samples are provided to the sample table 1 and arranged as shown in the chart in FIG. 3. The samples are processed, and for each sample, as many different analog signals are presented at terminal 30 as are programmed the selection board and control means 6. The operations of FIGS. 5-8 are performed identically for each channel representing one of the different outputs produced for one sample. For example, if there are 17 channels in the analyzer 1 of FIG. 1, the operation of FIGS. 5-8 is repeated 17 times for each sample listed in FIG. 3.

In order to provide the output indicative of a substance of the blood, each signal appearing at a terminal pair 30 obtained in response to measurement of a sample must be related to other data so that signal may be used to indicate the amount of substance for which a test is being done. This may be done identically for each channel. The output signal at the terminal 30 is indicative of the optical density of the liquid in the cuvette 26. For different chemistries to be performed, there is a predetermined relationship of optical density of the liquid at a specific wavelength, sometimes referred to as amount of color, to the amount of substance being tested for in the sample. Of course, the particular wavelength could as well be in the ultraviolet as well as in the visible range. For each chemistry, the inventors of the chemistry have found a relationship between optical density and concentration units. Generally, for usefulness on automatic analyzers, chemistries have been developed and curve-fitting has been done to substantially linearize the relationship between optical density and concentration units within the ranges of interest. Second order monotonic functions could also be used. However, the state of the prior art has not yet made this practicable. The use of such functions is wellknown, and forms no part of the present invention. What is necessary is that a reference optical density, hereinafter abreviated as ROD, be established for calibration purposes. Where a reference sample is used having a known number of concentration units of the particular substance therein is processed in that analyzer and there is a known function relating that concentration to the optical density, then there is a reference optical density, or ROD, corresponding to the electrical value of the output at the terminal pair 30. Other outputs from other samples at the terminal 30 may thus be related to this reference to indicate optical densities corresponding to other voltages. Commonly utilized circuitry such as log ratio amplifiers may be used to compensate for Beers Law non-linear relationships of output voltage to varying optical densities.

One particular function which has been useful with respect to established chemistries is:

$$R_{OD} = \frac{Cu}{A + BCu} + C \tag{1}$$

Where $Cu$ = concentration units obtained from the known reference value and where $A$, $B$ & $C$ are empirically obtained constants obtained such as by prior, commercially available curve-fitting computer programs such as are commercially available, for example, from Control Data Corporation. Once the reference OD is established, then the optical density of samples may be obtained by the relationship:

$$OD = \frac{K_{sam} - K_B}{K_R - K_B} R_{OD} \qquad (2)$$

Where $K_{sam}$ = the output obtained in response to an unknown sample;

$K_B$ = the value stored in memory based on measurements of samples in positions 101, 103 and 105 in FIG. 3 and selected as described with respect to FIGS. 5–8;

$K_R$ = the output stored in memory in response to measurement of samples 102, 104 and 106 in FIG. 3 and selected as described with respect to FIGS. 5–8;

$R_{OD}$ = the calculated reference OD stored in memory; and $OD$ = the optical density of the sample being measured.

Once an OD is known, then equation (1) may be solved for concentration units to give the result:

$$Cu = \frac{(OD - C) A}{(1 + CB) - B(OD)} \qquad (3)$$

The calculations of equation (3) derived by the solution of equation (1) are performed by prior art means. It is thus seen that the manner in which $K_R$ and $K_B$, the calibration values, are selected is critical in obtaining the proper output in concentration units from the automatic apparatus of the present invention. It is the selection of $K_R$ and $K_B$ that is referred to as calibration in the present context. Recalibration is also provided for, as indicated by the provisions of samples 117–119 in FIG. 3. Recalibration provides for adjustments due to drift.

Briefly, in the preferred form, the value of the readout obtained in response to samples 101, 103, and 105 or from samples 102, 104 and 106 are each given their turn for evaluation as $K_B$ or $K_R$ respectively. Results of utilization of the values are compared with preselected stored values. A valid value provides a result with a preselected level of error of the stored value. The most current valid value is used as $K_B$ or $K_R$. Alternatively, any valid value may be used as a calibration value.

The calibration control sample, such as 107 in FIG. 3, is utilized to provide test samples having known output values against which to measure the performance of processing circuitry based on the calibration, i.e., selection of $K_B$ and $K_R$. In order to provide the known concentration values, assay sheets may be provided for the blank, reference serum and calibration control serum samples. These values are entered into the memory 45 by entry on the data entry keyboard 8. Alternatively, initial values may be provided on a cassette in the cassette unit 48. These values are thus available when required as described with respect to FIGS. 5–8.

Figure 5:
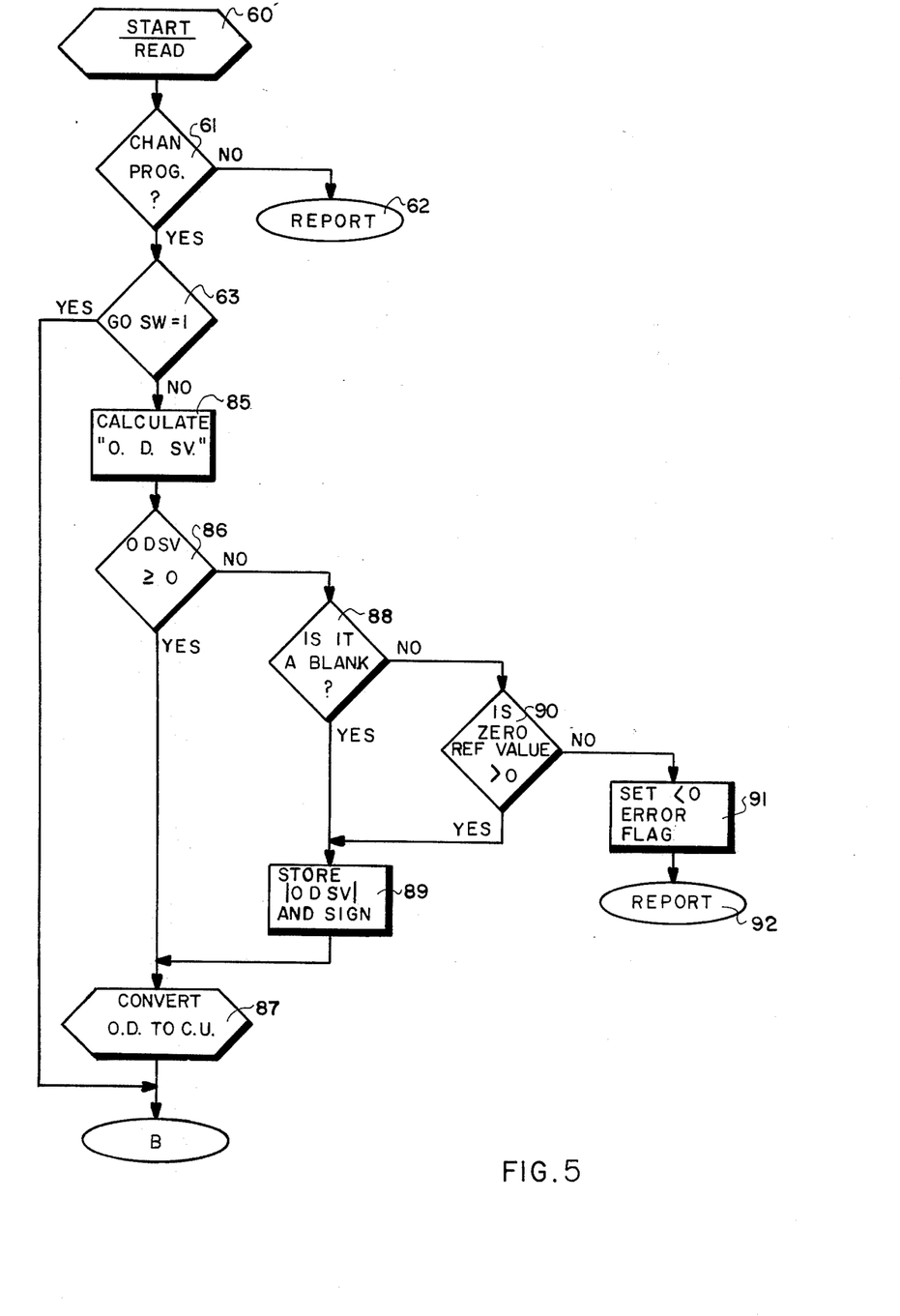
FIGS. 5 through 8 are flow diagrams useful in understanding the operation of the circuitry of FIG. 4.
Figure 6:
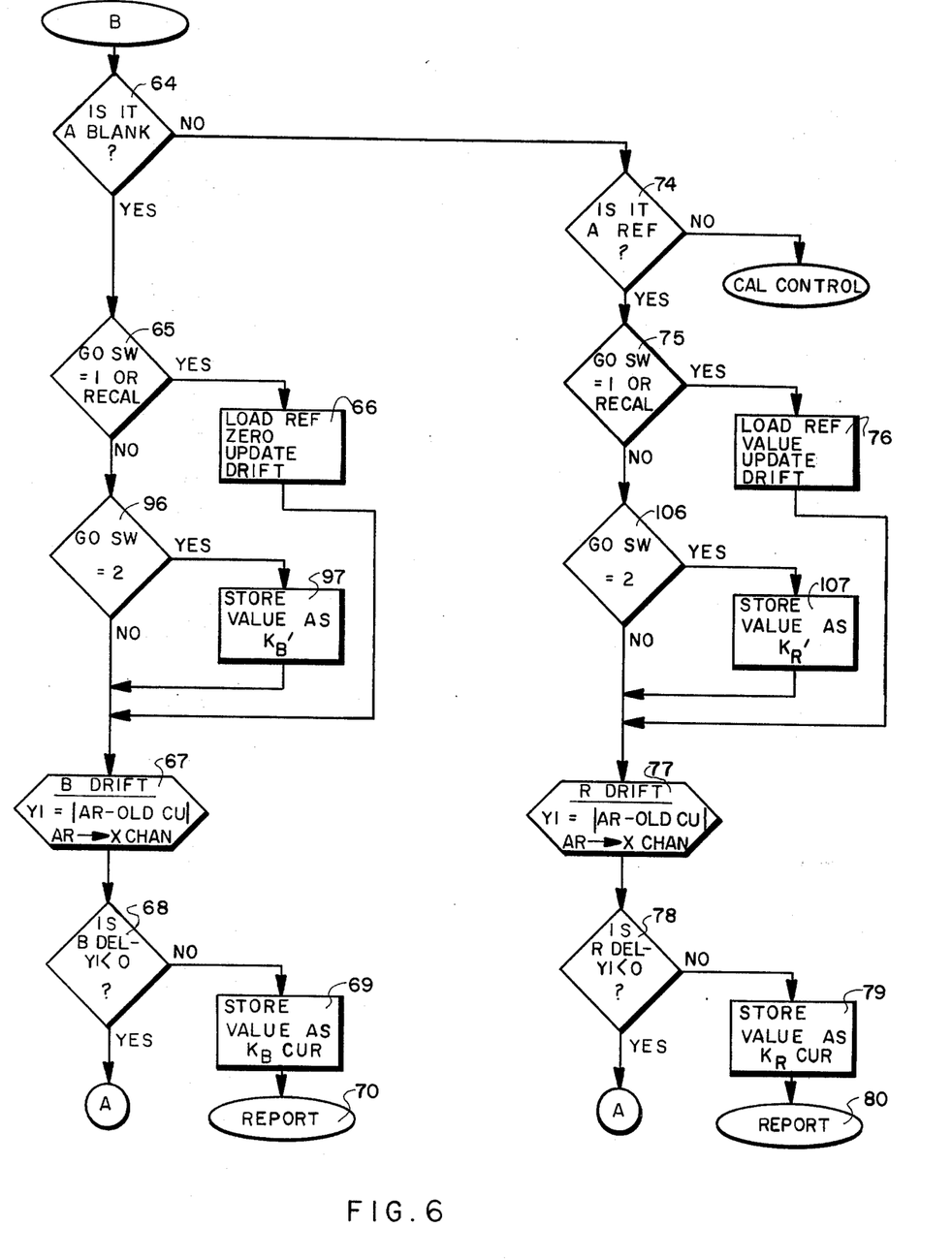

In FIGS. 5–8, the term GO-SW is utilized, and is short for Go-Switch. This is a register maintaining a count produced in response to entry of the identity of what is to be in successive positions as in the chart of FIG. 3. GO-Switch = 0 refers to a calibration control, data (i.e. from an unknown sample, or recalibration. Go-Switch = 1 is applied by the register when the first pair of calibration samples, 101 and 102 are provided. Similarly, Go-Switch = 2 and 3 respectively refer to the second and third pairs of calibration samples, the pair of 103 and 104 and the pair of 105 and 106. The object of the program is, of course, to provide an output value. The output value is provided by providing signals for connection to print-out or other utilization means. Thus the end of all the routines and accomplishment of the purpose of the present apparatus is indicated by progressing to the step Report. The connecting block B is seen at the end of FIG. 5 and beginning of FIG. 6 to indicate a progression of program. The terminals A in FIG. 6 indicate that progression is made to FIG. 7, and the cal control block in FIG. 6 is used to indicate that the next step is found at the beginning of FIG. 8.

The apparatus according to the present invention commences operation at block 60 in FIG. 5 which represents a subroutine START - READ. At this time, the input/output device 43 (FIG. 4) accesses available outputs from the analog-to-digital converter 36 via the input bus 40 and stores a value for each channel in a buffer register called VAL. At block 61 the determination as to whether the channel corresponding to each accessed output was programmed, such as by a depression of a button in the selection board included in the control means 6, and if not, such is reported at block 62. The signal provided at that output may be representative of a blank space. If at block 61, it is determined that the channel is programmed and the decision is made at block 63 as to whether the Go-Switch = 1. The alternative yes will be discussed first since at the initiation of operation, when samples in positions 101 and 102 are processed, the Go-Switch does indeed equal 1. This leads to the Terminal B at the bottom of FIG. 5, which leads to the Terminal B at the top of FIG. 6.

At block 64 a sample register storing the representation of the type of contents as indicated in FIG. 3 is consulted to determine whether the sample under consideration is a blank. At block 65, again another check is made to determine of the Go-Switch = 1, or if this is a recalibration. Since it is a blank, the system proceeds to block 66, which loads a baseline reference value input as described above from the keyboard 8 or cassette 48, which will be zero for some chemistries, in a register called T. In block 66, "UPDATE DRIFT" indicates that a value is loaded into a register called YI. The T and YI registers are temporary storage registers. When the Go-Switch equals 1, there has not been any drift, since there is no previous reading from which the system can have drifted. Therefore, a zero value is loaded into the YI register.

At block 67 following, a drift value is calculated. The drift is checked when Go-Switch is not equal to 1 by determining a value YI. The value in YI is the absolute value of the difference between the contents of an AR register at the time the check is made minus the previous concentration units reading, which will be accessed from an XCHAN register. However, when Go-Switch equals 1, a zero value has been provided to the YI register. Then the current contents of the AR register are loaded into the XCHAN register. The AR register is a working register, and the XCHAN register is a temporary storage register. At block 67 when the Go-Switch equals 1, the YI value is set equal to zero as just described above, and the baseline value is accessed from the T register and moved through the AR register to the XCHAN register.

At block 68, it is determined whether the drift exceeds allowable limits. Allowable limits have already been entered from the keyboard 8 or preferably the cassette 48 into the memory 45. The entered value B DEL has the value of YI subtracted therefrom. If the difference is greater than zero, there is no error beyond the limits which have thus been preselected, and the value obtained by the current reading of the blank from the analog-to-digital converter 36 is stored as $K_B$ CUR. This is a current value of $K_B$ and is saved in a temporary storage register called $K_B$ until subsequent determinations of $K_B$ are made for samples 103 and 105. One of these values will be used as $K_B$ for solution of sample values according to equation 2 above. If there is an error, then operation proceeds to terminal A in FIG. 7. It should be noted that separate VAL, T, YI, XCHAN, $K_B$, $K_{B'}$, $K_R$, and $K_{R'}$ (described below) are provided for each channel, thus providing for independent calibration capability for each channel.

Returning to block 64, (FIG. 6) if the Go-Switch equals 1 and the sample is not a blank, operation proceeds to block 74, and the sample register is checked to see if the current sample is a reference. If results are received from sample 102, it is a reference, and at block 75 the analysis is made as to whether the Go-Switch equals 1 or a recalibration is being made. Since the Go-Switch does equal 1 here, block 76 is proceeded to and an initial reference value as provided from the keyboard 8 or cassette 48 is loaded into the T register, and to update drift, an initial reference drift value, which is zero when Go-Switch equals 1, is loaded into the YI register for future use. Operation proceeds to block 77 at which reference drift is calculated. When Go-Switch is not equal to 1, the value of YI is calculated by taking the absolute value of the difference of the contents of the reference AR register at the time the check is made minus the contents of the XCHAN register. The reference value in the T register is moved through the AR register to the XCHAN register. When Go-Switch equals 1, the reference value is provided as the contents of the YI register. At block 68, it is decided if the difference between the allowable drift for the reference and the value of YI is less than zero. If so, there is an error and operation will proceed as explained with respect to FIG. 7. If not, then the measured value is stored as $K_R$ CUR; the current value in the VAL register is loaded in the $K_R$ register. At block 80 a report is made. A report normally consists of provision of a signal connected for providing a print-out of the reference value which was previously stored and the drift, which in the case of the Go-Switch equals 1 situation, will of course be zero, since there is no value from which the reading obtained will have drifted. This process is repeated for every channel of the sample.

At the beginning of the next machine cycle, block 60 (FIG. 5) is returned to and again, for each channel at block 61 the decision is made as to whether the channel is programmed, and if not, the report is provided as indicated at block 62. This time, at block 63, the answer to Go-Switch equals 1? is no, and operation proceeds to block 85 which in FIG. 5 is called calculate "OD SV" indicating the optical density value to be saved subject to the following tests.

$$OD\ SV = \frac{R_{OD}(VAL - B_{CUR})}{Y_{CUR} - B_{CUR}} \qquad (4)$$

where $VAL$ = the current measured value as stored in the VAL register, $B_{CUR}$ is the value of $K_B$ last saved, $Y_{CUR}$ is the value of $K_R$ last obtained.

At block 86 the value of OD SV is checked as to whether it is greater than or equal to zero. If so, as seen at block 87, OD is converted by the prior art processing means described above to concentration units in accordance with equation (3) above, and operation proceeds to FIG. 6. If not, operation proceeds to block 88 to check whether the value was produced in response to a blank. If so, at block 89 the absolute value of optical density obtained is stored as well as its sign, and operation proceeds back to block 87 at which concentration units are again calculated. It is possible for a blank to read less than zero. If it is not a blank, then operation proceeds from block 88 to block 90 at which the initial list of reference values provided by the keyboard 8 or cassette unit 48 is provided. The determination is made if the zero reference value is greater than zero. If so, then an OD not greater than zero could be obtained, and operation proceeds to block 89. If the zero reference value is less than or equal to zero, the operation proceeds from block 90 to block 91 which provides a "less than zero" error flag to the printing unit and consequently, as indicated at block 92, this error will be recorded in the report form.

Proceeding to FIG. 6, for the second blank, sample 103 in FIG. 3 at block 64 a yes decision will be made and at block 65 the answer to Go-Switch equals 1 or recalibration is no. The process of elimination is continued at block 96; of course in the third machine cycle, the answer to Go-Switch equals 2 is yes. The current value in the VAL register is stored as a value $K_{B'}$ in the $K_{B'}$ register as indicated at block 97. Block 67 is returned to to perform the drift check as specified above. YI is the difference between the contents of the AR register and "old-CU" or the concentration units obtained for the previous blank. When Go-Switch equals 2, the contents of the AR register during the drift check are the result of the processing at block 87 (FIG. 5). Since block 87 was not utilized when Go-Switch was equal to 1, "old CU" is equal to the previously entered value of the concentration units for the channel being processed from the keyboard 8 or cassette 48.

If the drift check at block 68 shows no error as defined above, then the current measured value of $K_B$ is stored as $K_B$ current by moving the value from the $K_{B'}$ register to replace the contents of the $K_B$ register. At block 69 this value is now stored as the candidate for calibration value $K_B$ for solving equation 2 later. Again, the current blank value from the AR register and the drift are reported at block 70.

Returning to block 64, for analysis of the sample in position 104, the answer to is it a blank will be no, and the answer to is it a reference at block 74 is yes. At block 75 the Go-Switch equals 1 or recalibrate determination will be no, to lead to block 106. At block 106, the determination of Go-Switch equals 2 is yes. As indicated at block 107, the current value from the VAL register is stored as $K_{R'}$ in the $K_{R'}$ register. Returning to block 77, the drift check specified above is made. YI is the difference between the contents of the AR register and "Old CU" or the concentration units obtained for the previous blank. When Go-Switch equals 2, the contents of the AR register during the drift check are the result of the processing at block 87 (FIG. 5). Since block 87 was not utilized when Go-Switch was equal to 1, "old CU" is equal to the previously entered value of the concentration units for the channel being processed from the keyboard 8 or cassette 48. Again at block 78 the reference drift is examined to see if it exceeds allowable limits. If not, the value is moved from the $K_{R'}$ register to replace the contents of the $K_R$ register to be stored as $K_R$ current as indicated at block 79, and a report is made at block 80 or reference concentration units and drift.

For the third calibration pair, the machine cycle for processing the sample in position 105 occurs and block 60 is again returned to. Again, at block 61 a check is made as to whether the channel is programmed. Operation proceeds through blocks 63 and 85 and 86, and on to block 64 as described above. For sample 105 the answer at block 64 to is it a blank will be yes, and the answer that blocks 65 and 96 to Go-Switch equals 1 or 2 will be no. The same drift calculation is made at block 87. Here, "Old CU" is that calculated at block 67 for sample 103. The drift check is made again at block 68. If there is no error, the value from the VAL register will be stored as $K_B$ current by replacing the contents in the $K_B$ register with the value, and it will be utilized as the calibration value of $K_B$ in equation 2 for the unknown samples. Again the report is made at block 80. Similarly, for the machine cycle for the sample at position 106, operation again proceeds through the steps in FIG. 5 as described above, returning to blocks 64 and 74 where the answer at block 74 to is it a reference is yes. Operation proceeds through block 75 and 106 to block 77. Here, "Old CU" is that calculated at block 77 for sample 104. At block 78, the drift check is made. If no error is indicated, the value from the VAL register is moved to replace the contents of the $K_R$ register at block 79 to become the calibration value $K_R$ for use in solution according to equation (2) above. Again at block 80 values and drift are reported. It is thus seen that if a drift check finds one value to be unsatisfactory, a previous value will be saved which is successful or useful, i.e., no error results.

Figure 7:
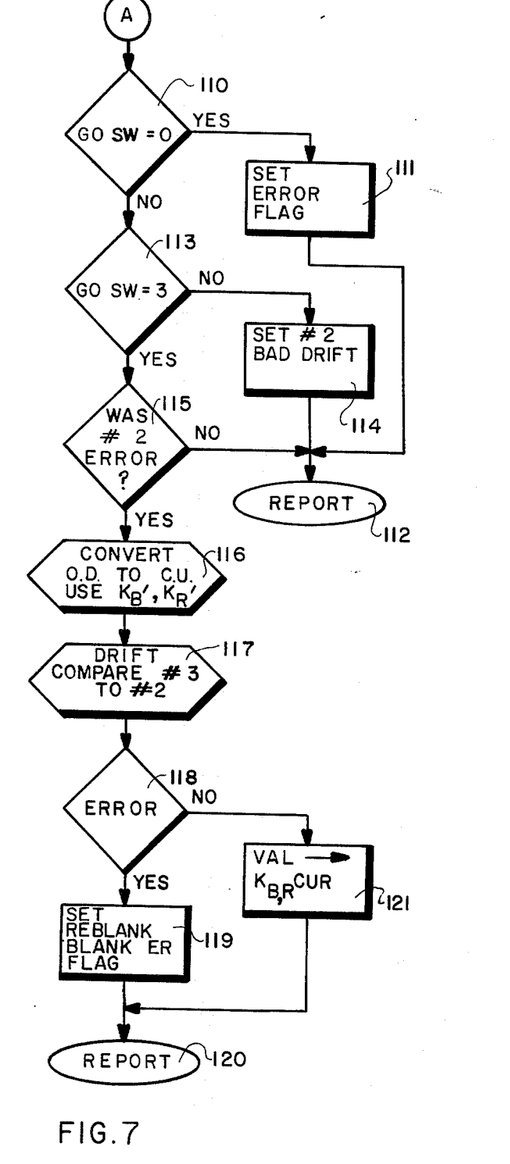

If an error occurs, the procedure is performed by the apparatus as indicated in FIG. 7. At block 110, the check is made as to whether the Go-Switch equals zero. If the answer is yes, then there is an error on the recalibration as is performed on samples 117-119 (FIG. 3), and as indicated at block 111, an error flag is set and reported as indicated at block 112. If the Go-Switch is not equal to zero, then the sample under consideration must be within the three initial pairs of calibration samples. At block 113, a check Go-Switch equals 3 is made to see if the sample is the second blank or reference or the third blank or reference, since there cannot be an error on the first blank or reference. If the answer to Go-Switch equals 3 is no, then the second blank or reference is being tested. As indicated at block 114, a drift error or set number two bad drift is indicated as the report step at block 112. If the Go-Switch equals 3. operation proceeds from block 113 to block 115, and the memory is checked to see if "Number 2" or the second blank or reference was in error. If not, then the value of $K_B$ or $K_R$ obtained on the third blank or reference is disregarded, and at block 112 any error is reported. However, as explained above, prior successful values of $K_B$ and $K_R$ have been stored for use as calibration values. As indicated at block 16, if there is an error at the second blank or reference, OD is converted to concentration units by equation (2) using previously stored values of $K_B$ and $K_R$. As indicated at block 117, the drift value obtained from the second blank or reference is compared to the value obtained from the drift value from the respective third blank or reference. It is thus determined if while there was a drift from the first blank or reference, it has stabilized with respect to the second and third blanks or references. As indicated at block 118, if an error is still present, then a blank or reference error flag is set at block 119 for reporting as indicated at block 120. If stabilization is indicated by lack of drift between samples from second and third calibration pairs, as indicated at block 118, the value in the VAL register is stored as a successful calibration value. This value of $K_B$ or $K_R$ may then be validly utilized for solution of equation (2) for the unknown samples.

Figure 8:
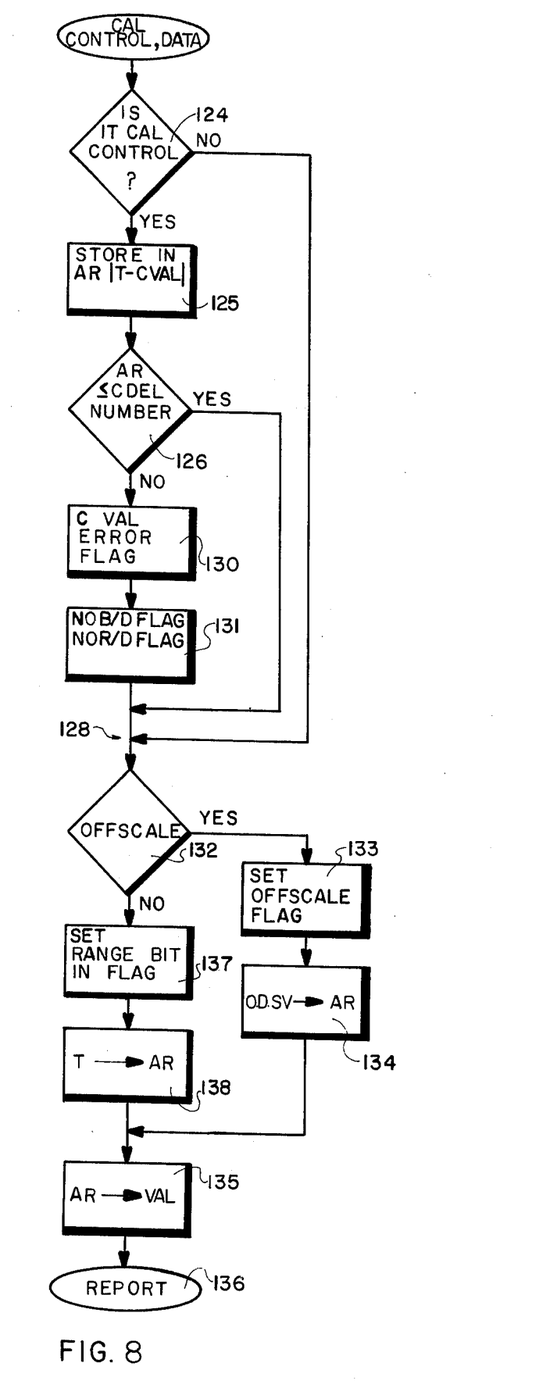

On all situations for calibration control as indicated for sample at position 107 in FIG. 3 or data which are output readings obtained in response to the samples labeled "sample" in FIG. 3, operation again returns to block 60 (FIG. 5) and leads through blocks of FIG. 5 through blocks 64 and 74 in FIG. 6, where the answer will be no, the sample is not a blank or a reference, leading to the cal control, data terminal, at the top of FIG. 8. If the sample under consideration is a cal control as indicated by block 124. Then at block 125 a value is stored in the AR working register, which is the absolute value of the difference between the value obtained and put in the T register from the result of block 87 (FIG. 5) and the value C VAL previously entered by the keyboard 8 or cassette 48. The value C VAL is a predetermined known result which should be obtained from the processing at block 87. As indicated at block 126, this difference is compared to a previously entered allowable error, C DEL also appropriately stored. If the difference is less than the allowable error, successful operation has been verified. Operation proceeds to terminal 128. If the number thus put in the AR register is not less than or equal to the permissible deviation, then the answer at block 126 is no, and failure to produce the predetermined correct result is indicated. A C VAL, or calibration control error flag is set for inclusion at the next report at block 131. At block 132 no blank drift or reference drift flag will be set. Thus the drift subroutine will not be called.

If the sample is not a calibration control but data, then the answer at block 24 is no, and terminal 128 is proceeded to directly. From terminal 128 it is determined whether the value obtained is off-scale according to a preprogrammed table for each chemistry at block 132. If so, at block 133, an off-scale flag is set, and the value of optical density previously saved at block 83 (FIG. 5) is loaded into the AR register as indicated at block 134. In this manner, the report will include a meaningful optical density result, even where a concentration unit result might not be meaningful. As indicated at block 135, the value of the optical density is loaded into the AR register for provision as report data as indicated at block 136. If the reading is not off-scale, then at block 137 the feature of providing a range bit set in a report form flat, such as an indication of whether the concentration unit value thus obtained in a high, medium or low range may be provided. This feature is further disclosed in commonly assigned copending patent application Ser. No 374,674 filed June 28, 1973 by Gerald Jay Stussman, et al. The range is determined by comparison of the concentration unit value with preprogrammed tables for each chemistry. The concentration unit value is loaded from the T register as indicated at block 138 to the AR register. The T register at this point has been storing the result of the calculation of block 81 (FIG. 5). Once this value is provided, then the concentration unit value which is within scale, is provided from the AR register to the VAL register for reporting as indicated at block 135.

It is thus seen that initial pairs of calibration sets are examined and the various useful values such as measured indication of the analog value from the terminal set 30 is saved, the concentration value value is saved until needed further, and the optical density value is saved until needed further. When the calibration is verified as satisfaactory by comparison to known values entered through the keyboard 8 or to cassette 48, then the most recent value for use in equation 2 is provided. When a drift specification is not met, the currently measured value cannot be used, but a previously measured value has been saved to be made available. After an interval of samples has been run, such as indicated at positions 108 through 116 in FIG. 3, then a recalibration may be made to update the value of $K_B$ and $K_R$ for use in equation 2. This is useful since, as the machine warms up, chemistries may tend to differ, and normal apparatus functions which may produce drift are also present. In this manner, reliable calibration is provided. If, on initial calibration or on recalibration, an unsuccesful calibration value is obtained, then such error is positively flagged. Previous good values of $K_B$ and $K_R$, if any, are available for use. The machine operator may examine the values obtained for possible use with the caveat that there was a problem. Such output information may be indeed useful to the operator as the cause of such unsuccessful recalibrations is often traceable. The various error flags inform the operator reviewing the report form exactly what current status of reliability of results is.

What is claimed as new and desired to be secured by Letters Patent of the United States is:

1. In an automatic chemical testing apparatus comprising readout means for producing readout signals indicative of optical density of samples wherein the wavelength at which optical density of a sample is measured is selected in correspondence with a particular chemistry being performed and the optical density at that wavelength is a function of the concentration of a particular substance therein for the particular chemistry, processing means for calculating a value of concentration units corresponding to the optical density indicated by the readout signal, wherein said processing means utilizes a predetermined curve function and wherein the predetermined curve function must be calibrated by the measurement of a blank sample and a reference sample each having a known concentration level of substances therein to provide calibration values indicative of a baseline and of a reference level for values of readout signals, and means for providing readout signals for a plurality of substantially identical blank samples and for a plurality of substantially identical reference samples, the improvement of means for providing calibration values to said processing means comprising: means for storing a first blank readout signal having a first blank value, means for storing a second blank readout signal having a second blank value, means supplying said second blank value to said processing means for obtaining a first blank concentration value based on the use of said second blank value as a calibration value, comparison means for measuring blank error between the first blank concentration value to a known stored blank concentration value for said blank sample, means responsive to said comparison means for supplying said second blank value to said processing means if the blank error is below a preselected level for providing said second blank value as a calibration value for processing of unknown samples.

2. The improvement according to claim 1 further comprising means for storinga first reference readout signal having a first reference value, means for storing a second reference readout signal having a second reference value, means supplying said second reference value to said processing means for obtaining a first reference concentration value based on the use of said second reference value as a calibration value, comparison means for measuring reference error between the first reference concentration value to a known stored reference concentration value for said reference sample, means responsive to said comparision means for supplying said second reference value to said processing means if the reference error is below a preselected level for providing said second reference value as a calibration value for processing of unknown samples.

3. The improvement according to claim 2 further comprising means responsive to said comparison means for providing an error flag output to utilization means when the blank or reference error exceeds the respective preselected level.

4. The improvement according to claim 3 for providing said first blank value as a calibration value when said blank error is above the respective preselected level and for providing said first reference value as a calibration value when the reference error is above the respective preselected level.

5. The improvement according to claim 4 further comprising means for processing a calibration control readout signal obtained in response to measurement of a calibration control sample in said processing means and utilizing the provided calibration values in said processing means to provide a calibration control concentration value, wherein said comparison means measures the calibration control concentration error between said calibration control value and a preset known calibration control value, and error sensing means responsive to said comparison means for indicating validity of said provided calibration values when said calibration control concentration error is below a preset level.

6. The improvement according to claim 5 further comprising means for providing an error flag to utilization means when the calibration control concentration error is above the preset level.

7. The improvement according to claim 6 further comprising means for storing a recalibration blank value and a recalibration reference value obtained from readout signals for a further blank and a further reference sample measured after processing of an interval of a number of unknown samples, means providing said recalibration blank and reference values to said processing means to provide respective first and second recalibration concentration values, means for comparing said first and second recalibration concentration values to said blank and reference concentration values, and means for replacing said calibration values with said further blank and further reference values when the respective comparisons indicate concentration value drift below a preset limit.

8. The improvement according to claim 7 further comprising means for processing a calibration control readout signal in response to a calibration control sample after processing said further blank and reference samples and comparing the concentration value obtained therefrom to a stored known recalibration concentration value for verifying validity of said further blank and reference values as calibration values.

9. The improvement according to claim 8 further comprising means for retaining said calibration values when the respective comparisons indicate concentration value drift above the preset limit.

10. The improvement according to claim 8 further comprising means for comparing a concentration value for each unknown sample to a stored range of values and means for providing said concentration value for each unknown sample to a stored range of values and means for providing said concentration value to utilization means when said concentration value lies within said range and means for providing a readout value indicative of optical density for the unknown sample and an off scale flag to said utilization means when the concentration value is not in the range.

11. In an automatic chemical testing apparatus comprising readout means for producing in each of a plurality of channels a readout signal indicative of optical density of an aliquot of a sample wherein the wavelength at which optical density of a sample aliquot is measured is selected in correspondence with a particular chemistry being performed and the optical density at that wavelength is a function of the concentration of a particular substance therein for the particular chemistry, processing means for calculating a value of concentration units corresponding to the optical density indicated by each of the readout signals, wherein said processing means utilizes a predetermined curve function for each channel and wherein the predetermined curve function must be calibrated by the messurement of a blank sample and a reference sample each having a known concentration level of substances therein to provide calibration values indicative of a baseline and of a reference level for values of readout signals, and means for providing readout signals for a plurality of substantially identical blank samples and for a plurality of substantially identical reference samples, the improvement of means for providing calibration values for each channel to said processing means comprising: means for storing a first blank readpout signal having a first blank value, means for storing a second blank readout signal having a second blank value, means supplying said second blank value to said processing means for obtaining a first blank concentration value based on the use of said second blank value as a calibration value, comparison means for measuring blank error between the first blank concentration value to a known stored blank concentration value for said blank sample, means for storing said second blank value, means for providing a third blank value to said processing means for obtaining a second blank concentration value, means for obtaining a second blank concentration value, said comparison means further being connected for measuring blank error between said second blank concentration value, and means for providing a successful blank value to said processing means, as a calibration value, where a successful value is one the use of which results in a blank error below a preselected level.

12. The improvement according to claim 11 further comprising means for storing a first reference readout signal having a first reference value, means for storing a second reference readout signal having a second reference value, means supplying said second reference value to said processing means for obtaining a first reference concentration value based on the use of said second reference value as a calibration value, comparison means for measuring reference error between the first reference concentration value to a known stored reference concentration value for said reference sample, means for storing said second reference value, means for providing a third reference value to said processing means for obtaining a second reference concentration value, means for obtaining a second reference concentration value, said comparison means further being connected for measuring reference error between said second reference concentration value, and means for providing a successful reference value to said processing means, as a calibration value, where a successful value is one the use of which results in a reference error below a preselected level.

13. The improvement according to claim 12 wherein said means for providing a successful blank value or reference value comprises means for providing the most recently obtained successful value.

14. The improvement according to claim 13 further comprising means for providing an error flag to utilization means when no blank value after said first blank value is a successful value and for providing the first blank value to said processing means as a calibration value.

15. The improvement according to claim 14 further comprising means for providing an error flag to utilization means when no reference value after said first reference value is a successful value and for providing the first reference value to said processing means as a calibration value.

16. The improvement according to claim 15 further comprising means for obtaining a further blank value and a further reference value and for producing a further blank concentration value and reference concentration value after an interval of processing of unknown samples, means for producing further blank error and reference error signals, and for replacing calibration values with the values of said further blank and reference signals if they are successful and for providing an error flag to utilization means if they are not.

17. In an automatic chemical testing method comprising in each of a plurality of channels a readout signal indicative of optical density of an aliquot of a sample wherein the wavelength at which optical density of a sample aliquot is measured is selected in correspondence with a particular chemistry being performed and the optical density at that wavelength is a function of the concentration of a particular substance therein for the particular chemistry, calculating in processing means a value of concentration units corresponding to the optical density indicated by each of the readout signals, wherein said processing means utilizes a predetermined curve function for each channel and wherein the predetermined curve function must be calibrated by the measurement of a blank sample and a reference sample each having a known concentration level of substance therein to provide calibration values indicative of a baseline and of a reference level for values of readout signals, and providing readout signals for a plurality of substantially identical blank samples and for a plurality of substantially identical reference samples, the improvement of a method for providing calibration values for each channel to said processing means comprising: obtaining a blank readout signal for each blank sample having a blank value, supplying each said blank value to said processing means for obtaining a respective blank concentration value based on the use of the said blank value as a calibration value, comparing selected ones of said blank concentration values for measuring blank error between blank concentration values, comparing at least one of said blank concentration values to a known stored blank concentration value, and supplying a successful blank value to said processing means as a calibration value, where a successful value is one the use of which results in a blank error below a preselected level.

18. The improved method according to claim 17 further comprising the steps of obtaining a reference readout signal for each reference sample having a reference value, supplying each said reference value to said processing means for obtaining a respective reference concentration value based on the use of the said reference value as a calibration value, comparing selected ones of said reference concentration values for measuring reference error between reference concentration values, comparing at least one of said reference concentration values to a known stored reference concentration value for said reference samples to obtain a further reference error value, and supplying a successful reference value to said processing means as a calibration value, where a successful value is one the use of which results in a reference error below a preselected level.

19. The improved method according to claim 18 wherein said step of providing a successful blank value or reference value comprises providing the most recently obtained successful value.

20. The improved method according to claim 19 further comprising providing an error flag to utilization means when no blank value after said first blank value is a successful value and providing the first blank value to said processing means as a calibration value.

21. The improved method according to claim 20 further comprising providing an error flag to utilization means when no reference value after said first reference value is a successful value and providing the first reference value to said processing means as a calibration value.

22. The improved method according to claim 21 further comprising obtaining a further blank value and a further reference value and for producing a further blank concentration value and reference concentration value after an interval of processing of unknown samples, producing a further blank error signal and a further reference error signal, and replacing calibration values with the values of said further blank and reference signals if they are successful and providing an error flag to utilization means if they are not.

* * * * *